(12) United States Patent
Miyamoto et al.

(10) Patent No.: US 8,029,779 B2
(45) Date of Patent: Oct. 4, 2011

(54) LACTIC ACID BACTERIA

(75) Inventors: Taku Miyamoto, Okayama (JP); Yoshio Naito, Nagoya (JP)

(73) Assignee: Biobalance Co., Ltd., Nagoya-shi (JP)

( * ) Notice: Subject to any disclaimer, the term of this patent is extended or adjusted under 35 U.S.C. 154(b) by 740 days.

(21) Appl. No.: 10/569,973

(22) PCT Filed: Mar. 4, 2005

(86) PCT No.: PCT/JP2005/003762
§ 371 (c)(1),
(2), (4) Date: Jun. 25, 2008

(87) PCT Pub. No.: WO2005/085418
PCT Pub. Date: Sep. 15, 2005

(65) Prior Publication Data
US 2008/0286406 A1 Nov. 20, 2008

(30) Foreign Application Priority Data

Mar. 4, 2004 (JP) ................................. 2004-059912

(51) Int. Cl.
*A61K 48/00* (2006.01)
(52) U.S. Cl. ......... 424/93.45; 426/6; 426/61; 435/252.9
(58) Field of Classification Search .................. None
See application file for complete search history.

(56) References Cited

FOREIGN PATENT DOCUMENTS

| JP | 64-86883 | | 3/1989 |
|---|---|---|---|
| JP | 8-298982 | | 11/1996 |
| JP | 8-298982 | A | 11/1996 |
| JP | 2001-299230 | | 10/2001 |
| JP | 2001-299230 | A | 10/2001 |
| JP | 2001-333766 | | 12/2001 |
| JP | 2001-333766 | A | 12/2001 |
| JP | 2002-291466 | | 10/2002 |

OTHER PUBLICATIONS

Schnürer et al., Trends in Food Science & Technology, 2005, vol. 16, p. 70-78.*

Japanese Office Action dated Aug. 14, 2008 (mailing date), issued in corresponding Japanese Patent Application No. 2004-059912.
Florianowicz, Teresu; "Antifungal activity of some microorganisms against *Penicillium expansum*"; Eur Food Res Technol, (2001) vol. 212, No. 3, pp. 282-286.
Florianowicz et al.; "Antifungal activity of some microorganisms against *Penicillium expansum*", European Food Research and Technology, vol. 212, No. 3, 2001, pp. 282-286. Cited in the ISR.
C. Artakul et al.; "Kobaki kassei o Yusuru Nyusankin no Tansaku to Dotei ni Tuite", The Japanese Society Zootechnical Science Annual Meetings abstracts, vol. 103, Mar. 20, 2004, p. 177. Cited in the ISR.
Erginaka et al.; "Antifungal activity of several lactic acid bacteria and bifidobactgeria", Arch.Lebensmittelhug, vol. 55, No. 3, Aug. 18, 2004, pp. 52-55. Cited in the ISR.
Lavermicocca et al.; "Purification and Characterization of Novel Antifungal Compounds from the Sourdough *Lactobacillus plantarum* Strain 21B", App. Environ. Microbiol., vol. 69, No. 1, 2000, pp. 4084-4090. Cited in the ISR.
Magnusson et al.; "Broad and complex antifungal activity among environmental isolates of lactic acid bacteria"; FEMS Microbiol Lett., vol. 219, No. 1, Feb. 14, 2003, pp. 129-135. Cited in the ISR.
International Search Report dated Jun. 21, 2005 of PCT/JP2005/003762.
Chinese Office Action dated Mar. 6, 2009, issued in corresponding Chinese Patent Application No. 200580007044.
Communication Pursuant to Article 94(3) EPC dated Jan. 14, 2008, issued in corresponding European Patent Application No. 05720034.7.
Florianowicz, T.; "Antifungal activity of some microorganisms against *Penicillium expansum*"; European Food Research and Technology; vol. 212, No. 3, 2001, pp. 282-286.
Communication pursuant to Article 96(2) EPC dated Aug. 22, 2007, issued in corresponding European Patent Application No. 05720034.7.

* cited by examiner

*Primary Examiner* — Kade Ariani
(74) *Attorney, Agent, or Firm* — Westerman, Hattori, Daniels & Adrian, LLP

(57) ABSTRACT

*Lactobacillus delbrueckii* having antifungal activity is provided as novel lactic acid bacteria having antifungal activity. The *Lactobacillus delbrueckii* is *Lactobacillus delbrueckii* ANTI MUFFA FERM BP-10663 (FERM P-19705). The *Lactobacillus delbrueckii* has antifungal activity against mold of genus *Penicillium* and is excellent in probiotic activity even when used solo.

14 Claims, 5 Drawing Sheets

[Fig. 1]
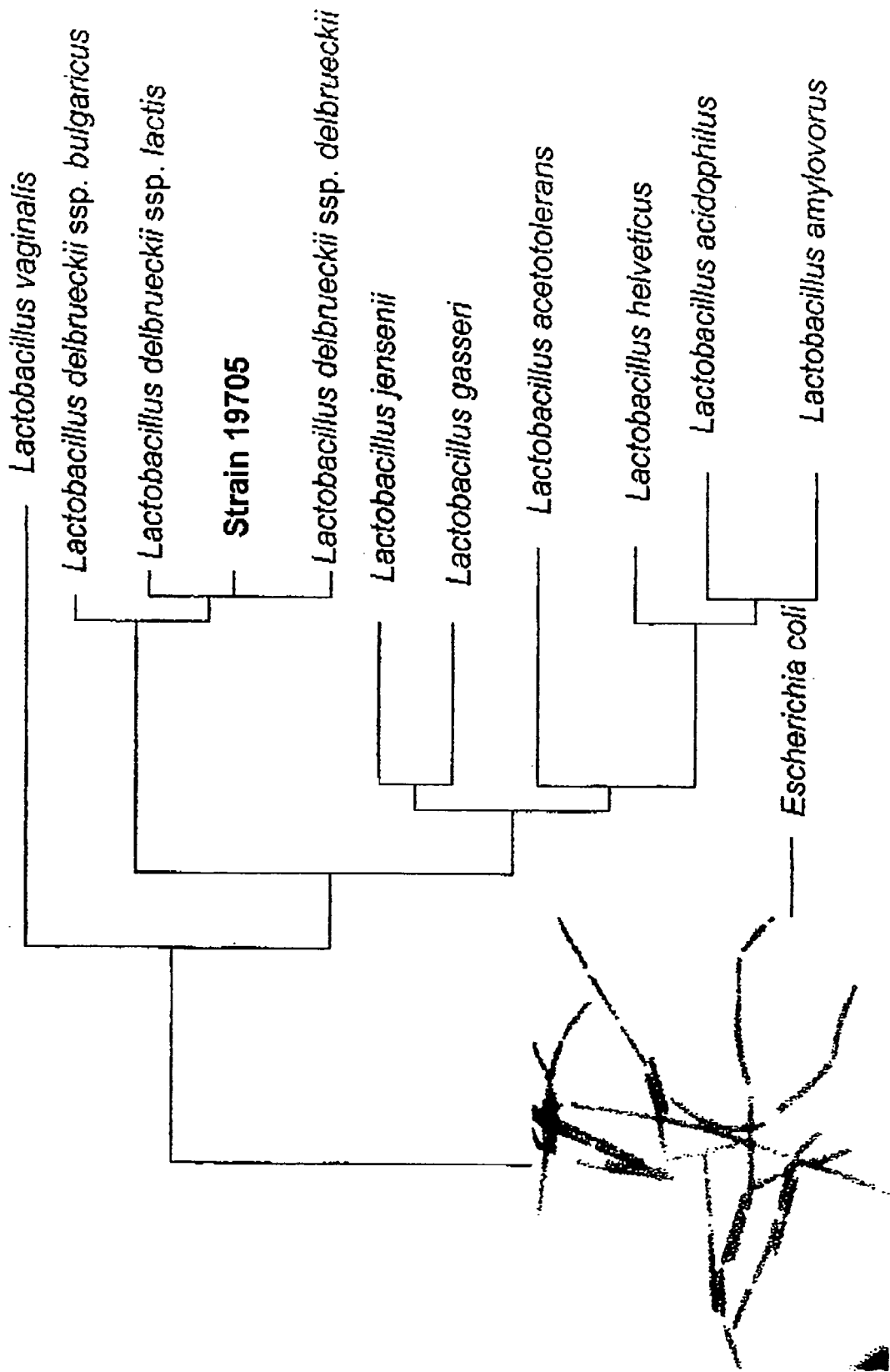

[Fig. 2]
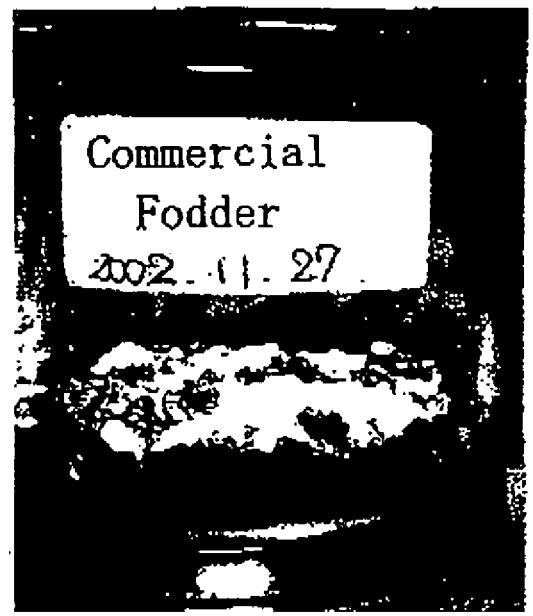
[Fig. 3]

[Fig. 4]
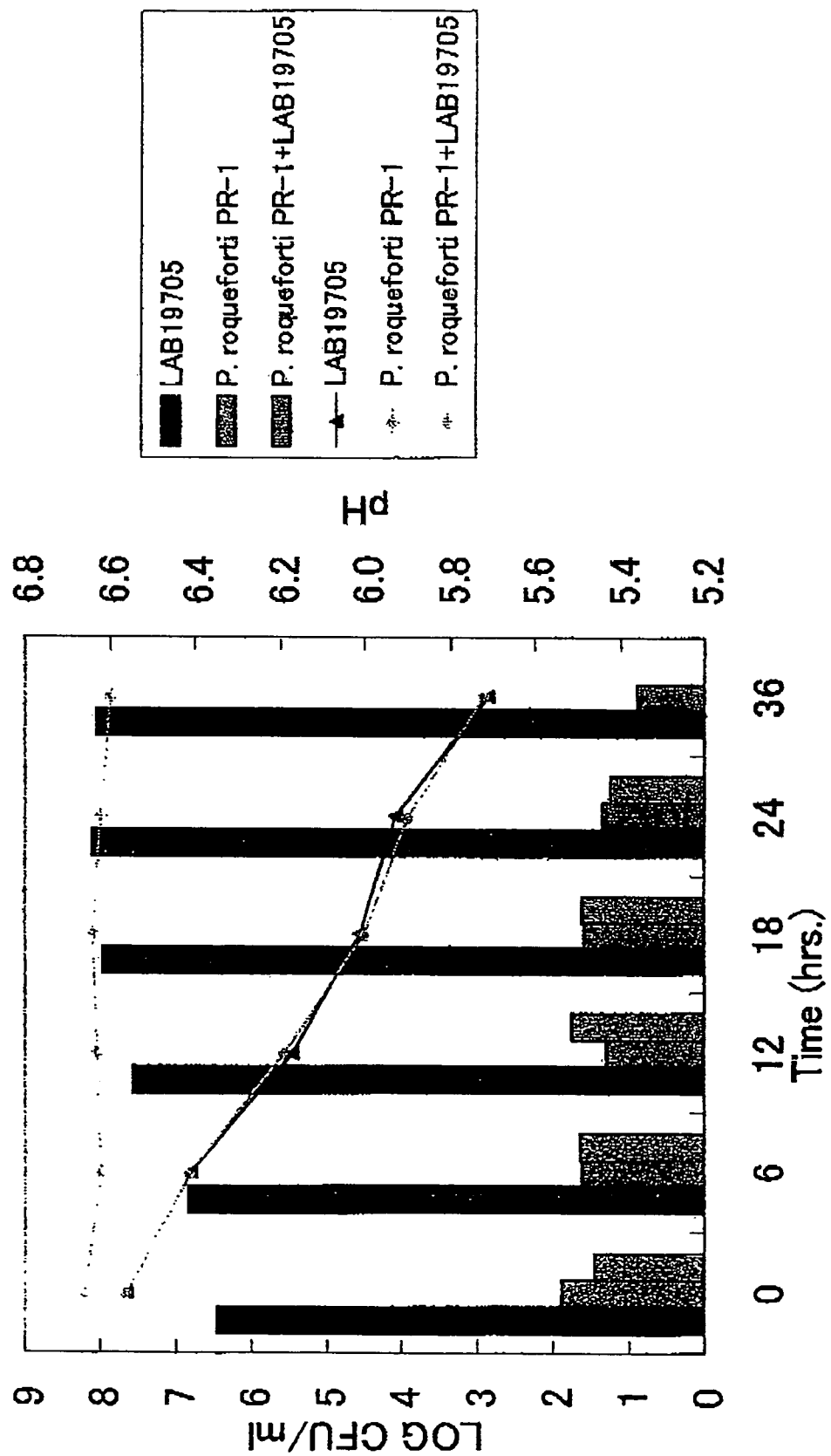

[Fig. 5]

[Fig. 6]
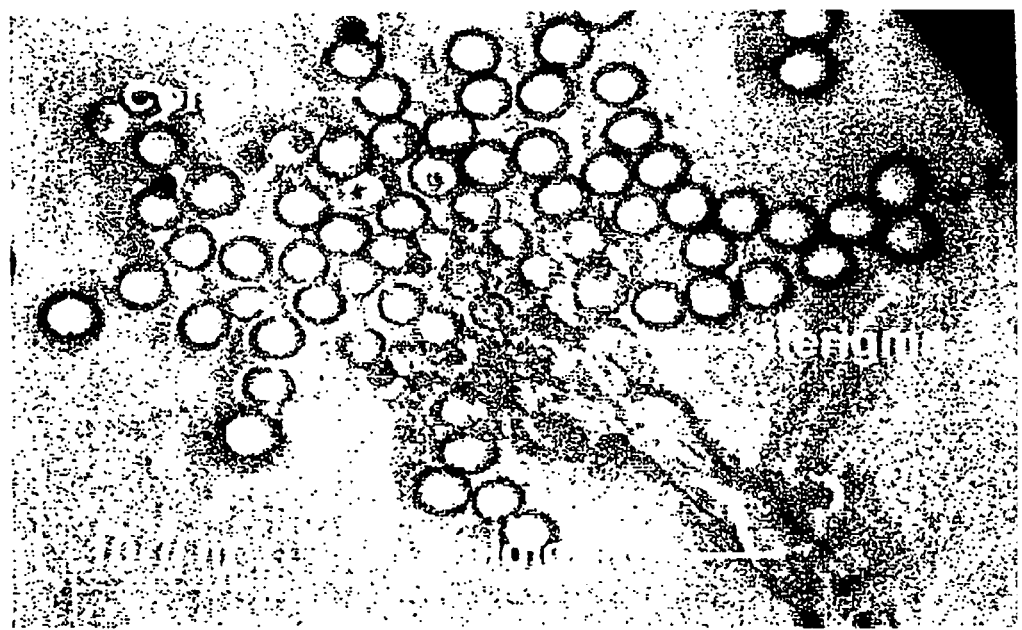
[Fig. 7]
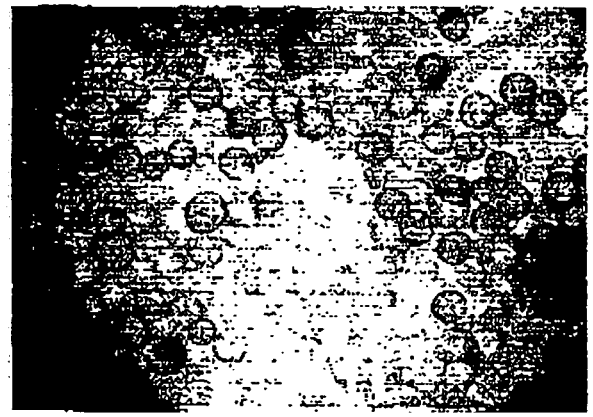
A
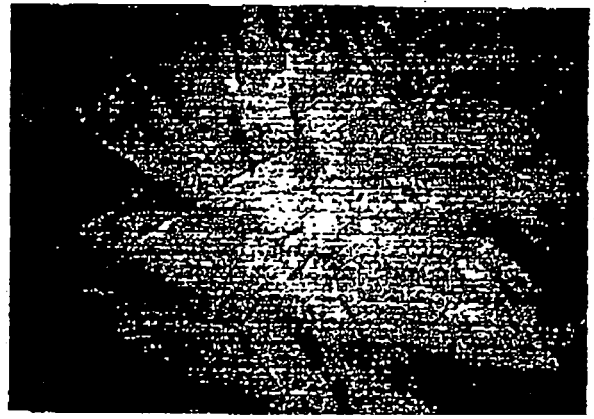
B

LACTIC ACID BACTERIA

TECHNICAL FIELD

This invention relates to novel lactic acid bacteria that have antifungal activity and that are excellent in probiotic activity.

BACKGROUND ART

Lactic acid bacteria are known to produce a variety of antimicrobial substances (antibacterial substances) such as a lactic acid, an organic acid, a volatile fatty acid, a hydrogen peroxide, a benzoic acid, a bacteriocin (niacin, colicin or the like) and so on. The lactic acid bacteria are used not only for a dairy starter but also for preservation of foods (biopreservation) by use of an antibacterial activity. However, not only bacteria propagate themselves as pathogenic bacteria or putrefactive bacteria, but also mold propagates itself during the preservation of the foods. Thus, most of the lactic acid bacteria were not effective against propagation of the mold. Particularly, the mold tends to propagate itself on an animal feed. Therefore, an intake rate of the feed for animals was sometimes lowered because of heat generation or bad smell of the feed caused by the propagation of the mold. In addition, a hopper opening of a feed tank sometimes clogged up by the propagation of the mold thereby blocking the feed from discharging. On the other hand, an antibiotic substance having an antifungal activity or an antifungal agent such as a formic acid was sometimes added in the animal feed in order to prevent and remove the propagation of the mold. However, there were a problem that the antifungal agent caused erosion and problems that the antibiotic substance caused the animals diarrhea or indigestion or caused emergence of drug-resistant bacteria or abnormal intestinal flora or the like to the animals. Conventionally, lactic acid bacteria having the antifungal activity are little known except *Lactobacillus sanfranciscencis* (refer to Patent Publication No. 1) and *Lactobacillus plantrum* (refer to Non-Patent Publication No. 1).

Conventionally, the lactic acid bacteria are also used as probiotics. As such ones, there are many proposals: a veterinary medication containing *lactobacillus salivarius* (refer to PATENT PUBLICATION 2), a deodorant feed containing at least 0.1% of mixed microorganisms mainly compose of more than N×106 of lactic acid coccus and sporeformer (refer to Patent Publication No. 3), a feed additive adding an antioxidant substance and living microbial agent to a high-class organic matter, putting them in an airtight container and fermenting them under a temperature of 25° C. (centigrade) to 37° C. (centigrade) (refer to Patent Publication No. 4) and so on. "Probiotics" are also called a living microbial agent. According to the most common definition, it is a "living microbial additive that works beneficially on a host animal by improving a balance of an intestinal microbes" (Fuller, R.: Probiotics in man and animals. J. Appl. Bacteriol., 66, 365-378 (1989)). However, in these days, it may also be used in a broad sense as "microorganisms that beneficially work on health maintenance of a host" (Lee, Y. K. and Salminen, S.: The coming of age of probiotics, Trends Food Sci. Technol. 6, 241-245 (1995)). Thus, there is also a thought that even killed bacteria are included in the probiotics (Salminen, S. et al.: probiotics: how should they be defined?, Trends Food Sci. Technol., 10, 107-110 (1999)). Typical microorganisms as the probiotics are lactic acid bacteria including bifidobacteria. In addition, *bacillus subtilis*, butyric acid bacteria, propionic acid bacteria, yeast and the like are also used as the probiotics.

PATENT PUBLICATION NO. 1: Japanese Laid Open Patent Publication No. 2002-291466
NON-PATENT PUBLICATION NO. 1: Paola Lavermicocca et al. Applied and Environmental Microbiology, September 2000, p4084~p4090, vol. 66, No 9)
PATENT PUBLICATION NO. 2: Japanese Laid Open Patent Publication No. S50-132115
PATENT PUBLICATION NO. 3: Japanese Laid Open Patent Publication No. H9-322714
PATENT PUBLICATION NO. 4: Japanese Laid Open Patent Publication No. 2001-299230

DISCLOSURE OF THE INVENTION

Problems to be Solved by the Invention

However, there has been no report about *Lactobacillus delbrueckii* having antifungal activity until now. There is a suggestion to use the lactic acid bacteria alone about the lactic acid bacteria used as conventional probiotics as described in the Patent Publication No. 2. Still, a sufficient effect has not been acquired. Therefore, as mentioned above, the majority is occupied by the one using the lactic acid bacteria in combination with the other microorganisms or the one combining other useful materials. Lately there is little suggestions on the lactic acid bacteria capable of obtaining sufficient probiotics solo.

In view of the above-mentioned circumstances, an object of the present invention is to provide novel lactic acid bacteria that have antifungal activity and that are excellent in probiotic activity even in case of use solo.

Means to Solve the Problems

In order to solve the above-mentioned problem, novel lactic acid bacteria according to a first aspect of the present invention has a subject matter in *Lactobacillus delbrueckii* having antifungal activity.

*Lactobacillus delbrueckii* ANTI MUFFA (FERM P-19705) is preferable as the *Lactobacillus delbrueckii*.

*Lactobacillus delbrueckii* preferably consists of *Lactobacillus delbrueckii* having antifungal activity against *Penicillium* mold.

An animal feed according to a second aspect of the present invention is added with the aforementioned *Lactobacillus delbrueckii*.

An animal drink according to a third aspect of the present invention is added with the aforementioned *Lactobacillus delbrueckii*.

Living lactic acid bacteria agent according to a fourth aspect of the present invention has the aforementioned *Lactobacillus delbrueckii* as an active ingredient.

An animal feed additive according to a fifth aspect of the present invention has the aforementioned *Lactobacillus delbrueckii* as an active ingredient.

An improving method of animal breeding according to a sixth aspect of the present invention uses the aforementioned *Lactobacillus delbrueckii*.

An improvement of the animal breeding is preferably one of an improvement of deodorization of an excretory substance of animals, an improvement of a survival rate of animals, an improvement of an egg-laying rate of hens for egg collection and an improvement of milk quality of milk cows. However, the improvement of the animal breeding broadly contains and includes effects acquired by the probiotic activity that the lactic acid bacteria of the present invention have.

A fermented food according to a seventh aspect of the present invention is manufactured by use of the aforementioned *Lactobacillus delbrueckii*.

A manufacturing method of a fermented food according to an eighth aspect of the present invention uses the aforementioned *Lactobacillus delbrueckii*.

A preservation method of a fermented food according to a ninth aspect of the present invention uses the aforementioned *Lactobacillus delbrueckii*.

A cleaning method of a stable according to a tenth aspect of the present invention disperses the aforementioned *Lactobacillus delbrueckii* on a floor or a ground of the stable.

A cleaning method of a water according to an eleventh aspect of the present invention disperses the aforementioned *Lactobacillus delbrueckii* directly into the water or houses them in a permeable case so as to immerse and deposit them in the water.

Effects of the Invention

Since the novel lactic acid bacteria according to the present invention have the antifungal activity, the novel lactic acid bacteria are useful for controlling the mold during preservation of foods, controlling the mold of animal feeds or the like. Consequently, it is possible to reduce problems caused by adding antibiotic substances or antifungal agents. Moreover, since the novel lactic acid bacteria according to the present invention are excellent in the probiotic activity, the novel lactic acid bacteria improve the intestinal flora. Consequently, they improve breeding of a host such as a domestic fowl or a domestic animal. In addition, the same effects are performed in the animal feed, the animal drink, the living lactic acid bacteria agent, the animal feed additive, the improvement method of the animal breeding, the fermented food, the manufacturing method of the fermented food, the preservation method of the food, the cleaning method of the stable and the cleaning method of the water each using the above-mentioned novel lactic acid bacteria.

BRIEF DESCRIPTION OF THE DRAWINGS

FIG. 1 shows a phylogenetic system of *Lactobacillus delbrueckii* ANTI MUFFA (FERM P-19705) by 16S rDNA gene sequence analysis.

FIG. 2 is a picture image showing a livestock feed of a first comparative example.

FIG. 3 is a picture image showing a livestock feed of a first practical example.

FIG. 4 is a graph showing a temporal change of antifungal activity and pH in 10% skim milk of *Lactobacillus delbrueckii* ANTI MUFFA (FERM P-19705) according to the present invention while compared with those of a comparative example (Examination Case No. 4).

FIG. 5 is a picture image showing antifungal activity in case of adding *Lactobacillus delbrueckii* ANTI MUFFA (FERM P-19705) according to the present invention to a feed while compared with that of a comparative example (Examination Case No. 5).

FIG. 6 is a photomicrograph image showing contaminated green mold isolated from the feed of the comparative example in FIG. 5.

FIG. 7 is a picture image showing antifungal activity in case of adding *Lactobacillus delbrueckii* ANTI MUFFA (FERM P-19705) according to the present invention to a feed while compared with that of a comparative example (Examination Case No. 6).

BEST MODE FOR CARRYING OUT THE INVENTION

*Lactobacillus delbrueckii* of the present invention is preferably *Lactobacillus delbrueckii* ANTI MUFFA, which may be referred to as "present bacteria" or "present strain" hereafter. This strain has been deposited in National Institute of Advanced Industrial Science and Technology, Patent Deposit Center (Central 6, 1-1-1, Tsukuba, Ibaraki Japan), on Feb. 27, 2004 under accession number FERM P-19705, and transferred from FERM P-19705 and deposited under accession number FERM BP-10663 at International Patent Organism Depository (IPOD), National Institute of Advanced Industrial Science and Technology, Tsukuba Central 6, 1-1-1 Higashi, Tsukuba, Ibaraki, 305-8568, Japan on Aug. 15, 2006.

The present bacteria were discovered in searching antibacterial activity of lactic acid bacteria. As shown in FIG. 1, the present bacteria has 99.5% homology to *Lactobacillus delbrueckii* subspecies *Lactis* (*Lactobacillus delbrueckii* subsp. *Lactis*) as a result of a lineage analysis by 16s rDNA base sequence analysis. Thus, it is thought to be a strain that belongs to *Lactobacillus delbrueckii* subspecies *Lactis* (*Lactobacillus delbrueckii* subsp. *Lactis*). Hereunder shown are mycological characteristics of the *Lactobacillus delbrueckii* ANTI MUFFA (FERM P-19705) cultivated by use of a liquid culture medium for passage of lactic acid bacteria, which had a distilled water added to 5.0 g of glucose, 5.0 g of lactose, 10.0 g of tryptone, 5.0 g of yeast extract, 1.0 g of Tween 80 and 9.1 g of L-cysteine hydrochloride into a total amount of 1000 ml and which was sterilized by a process of steaming under pressure at 121° C. for 15 minutes after being adjusted to pH6.8 to pH7.0. With respect to sugar assimilation, it was cultivated by use of a basal medium for sugar fermentability test, which had a distilled water added to 10.0 g of tryptone, 5.0 g of yeast extract and 0.06 g of bromcresol purple into a total amount of 1000 ml and which was sterilized by a process of steaming under pressure at 121° C. (centigrade) for 15 minutes after being adjusted to pH6.8.

Cell Shape: *Bacillus*, Spore Formation: Nil, Mobility: Nil, Gram Stain: +(plus), Behavior against Oxygen: Facultative Anaerobic, Growth at 15° C.: −(minus), Growth at 45° C. (centigrade): +(plus), Lactic Fermentation: Homo−(minus), Gas Generation from Glucose: −(minus), Ammonia Generation from Arginine: −(minus), Hydrolyzability of Sodiumu Hippurate: −(minus), Tolerance to 4% Sodium Chloride: −(minus), Sugar Assimilation: Arabinose−(minus), Xylose−(minus), Rhamnose−(minus), Ribose−(minus), Glucose+(plus), Mannose+(plus), Fructose+(plus), Galactose+(plus), Sucrose+(plus), Maltose+(plus), Cellobiose+(plus), Lactose+(plus), Trehalose+(plus), Melibiose−(minus), Raffinose−(minus), Melezitose−(minus), Mannitol−(minus), Sorbitol−(minus), Esculin+(plus), Salicin+(plus), Amygdalin−(minus), Sodium Gluconate−(minus), Produced Lactic Acid: D-Lactic Acid, Stereoisomerism of Produced Lactic Acid (HPLC, 24 Hrs): D(−)(90.7%), L(−)(9.3%), DNA GC Content (HPLC): 48.7%

The present bacteria can be incubated by use of an MRS medium, a TYLG medium, a milk medium or the like which is common to the incubation of the lactic acid bacteria. An incubation temperature is at 20° C. (centigrade) to 50° C. (centigrade), preferably at 30° C. (centigrade) to 40° C. (centigrade). An incubation pH is at 3.5 to 9.0, preferably at pH 4.5 to 7.0. An incubation time is preferably for 6 to 30 hours. The present bacteria have antifungal activity, particularly, antifungal activity against *Penicillium* mold. The present bacteria have a blocking function against *Penicillium olsonii* that easily breeds in an animal feed. Moreover, the present bacteria have a blocking function against *Penicillium chrysogenum* and *Penicillium roquefortii* having mycotoxin (fungal toxin) producibility. Furthermore, the present strain strongly controls or inhibits growth of *Kluyveromyces marxianus* variety lactis (*Kluyveromyces marxianus* var. *lactis* 5Y307).

The present bacteria are added for use in a livestock feed for domestic fowls, cattle, swine or the like, a pet feed for dogs, cats or the like, an aquaculture feed for fish such as eels or the like, so as to control or inhibit the mold of the feed by the antifungal activity thereof. Moreover, the present bacteria may be added in a drink such as drinking water for domestic fowls, domestic animals or pets.

The present bacteria can be used for a living or viable lactic acid bacteria agent that has the present bacteria as an active ingredient. The viable lactic acid bacteria agent may be commonly prepared by the present bacteria alone. Alternatively, it may be mixed with a substance as a nutrient source of the present bacteria, such as corn, bran, rice bran or the like. In addition, the living lactic acid bacteria may be used in combination with other microorganisms or other useful materials that may not block or disturb the growth of the present bacteria. The living lactic acid bacteria can be added for use in the animal feed or the animal drink.

The present bacteria satisfy safety, so that it is applicable to a starter for fermented foods. Moreover, the present bacteria have the antifungal activity, so that it is added so as to control and prevent pathogenic bacteria or putrefactive bacteria. Thus, the present bacteria can be used for preservation of foods.

In addition, the present bacteria can be used as probiotics. Probiotics are defined as orally ingestible microorganisms that bring about beneficial effects on a host by improving intestinal flora of the host. The beneficial effects brought about to the host means a variety of effects that are obtained by ingestion of animals: promotion of animal growth, improvement of a feed demand rate, prevention and betterment of enteropathy, deodorization of excretory substances, improvement of survival rate, increase in egg-laying rate of egg collection chickens, improvement of milk quality of milk cows or the like. It has the same meaning as improvement of animal breeding. The present bacteria is able to improve the animal breeding by the probiotic activity by making the animals ingest the animal feed added with an animal feed additive having the present bacteria as the active ingredient.

First Practical Example

While the present invention is described in detail while showing practical examples, the present invention is not limited to the following practical examples.

Manufacturing Example

The present bacteria were inoculated in a MRS medium and incubated at 30° C. (centigrade) to 40° C. (centigrade) for 24 hours for primary culture. Then, a culture fluid was sprayed on a sterilized bran and incubated at 30° C. (centigrade) to 40° C. (centigrade) for three days for secondary culture so as to obtain a living lactic acid bacteria agent. A bacterial count of the present bacteria contained in the acquired living lactic acid bacteria agent was $5.3*10^9$/g.

[Examination Case No. 1 of Antifungal Activity]

Mold spores of a test bacterial strain in Table 1 was smeared on a skim-milk agar plate (10 ml of sterilized 10% skim-milk, 5 ml of 2% agar dissolved with BCP (100 mg/l), 150 μl (micro liter) of TYLG culture fluid (containing $10^6$/ml of the present bacteria)). Then, 5 ml of 0.15% soft agar added with 50 μl (micro liter) TYLG (containing the $10^6$/ml of the present bacteria) was overlaid thereon. Thereafter, the bacteria were cultured at 30° C. (centigrade) for 2 days. After the culture, a blocking function against propagation of the mold was assessed in comparison with a control having no mold spores smeared thereon. As a result, as shown in Table 1, it showed a strong inhibiting function against the mold of the genus *Penicillium*.

TABLE 1

| Kind of Mold | Blocking Function of Antifungus |
|---|---|
| *Aspergillus flavus* variety *flavus* (*Aspergillus flavus* var. *flavus*, JCM10252) | − (minus) |
| *Aspergillus niger* (*Aspergillus niger*, JCM5546) | − (minus) |
| *Aspergillus oryzae* variety *oryzae* (*Aspergillus oryzae* var. *oryzae*, JCM2239) | − (minus) |
| *Fusariumu oxysporum* f. species *cucumerinum* (*Fusariumu oxysporum* f. sp. *cucumerinum*, JCM9284) | − (minus) |
| *Geotrichum candidum* (*Geotrichum candidum*, JCM1747) | − (minus) |
| *Penicillium candidum* (*Penicillium candidum*, SAM-2) | − (minus) |
| *Penicillium chrysogenum* (*Penicillium chrysogenum*, JCM2056) | + (plus) |
| *Penicillium olsonii* | + (plus) |
| *Penicillium roqueforti* (*Penicillium roqueforti*, PR-2) | + (plus) |
| *Rhyzopus oryzae* (*Rhyzopus oryzae*, JCM 5557) | − (minus) |

[Examination Case NO. 2 of Antifungal Activity (First Practical Example]

A test was conducted whether it was possible to control and inhibit propagation of mold on a livestock feed by adding the present bacteria to the livestock feed. One gram ($5.3*10^9$ in number) of the living lactic acid bacterial agent obtained in the aforementioned manufacturing example was added to 20 gram of the animal feed (60 wt % of cereal (corn, rye), 26 wt % of oil-seed cake and meal, 2 wt % of chaff and bran and 12 wt % of other materials (sweet stuff waste, molasses or the like)). Then, such animal feed was added with 20 ml of distilled water and left out for 377 days at room temperature while housed in a cup (First Practical Example). 20 gram of a similar livestock feed was added only with 20 ml of distilled water and left out in the same manner (First Comparison Example). As a result, as shown in FIG. 2 and FIG. 3, *Penicillium olsonii* as contaminated mold of the livestock feed propagated on the feed and the feed changed color in blue green in the first comparative example. In contrast, the *Penicillium olsonii* was controlled and prevented from propagation in the first practical embodiment. The first comparative example in FIG. 2 shows a state after 31 days from the neglect, while the first practical embodiment 1 in FIG. 3 shows a state after 377 days from the neglect.

[Examination Case No. 3 of Antifungal Activity]

An examination was conducted on antifungal activity of the present strain that was screened by a milk agar plate method. A *Penicillium roqueforti* PR-1 strain, which may be referred to as "PR-1 strain" hereafter, was used as an indicator mold. First, 10 ml of 10% skimmed milk, 5 ml of 2% agar solution containing BPC (100 mg/l) and 150 μl of the culture fluid of the present strain were mixed. After the agar hardened, mold spores of the PR-1 strain that was diluted ten times was smeared thereon. In preparing the mold spores, a potate dextrose agar slant medium cultured at 25° C. (centigrade) for 7 days was added with normal saline solution containing Tween 80 (0.1%) and stirred thereafter. Then, there were provided for test spores prepared by filtration through a glass wool.

Next, 5 ml of a soft agar (0.15%) added with 50 µl (micro liter) of a culture fluid of the present strain culture was overlaid thereon and incubated at 30° C. (centigrade) for 2 to 5 days. Consequently, it was confirmed that growth of the mold (PR-1 strain) was obviously restrained in a culture medium (test plate) containing the present strain having the antifungal activity in comparison with a culture medium (control plate) that cultivated the mold (PR-1 strain) solo. Thus, a degree of growth of the mold (PR-1 strain) was compared between the control plate and the test plate, thereby measuring the antifungal activity of the present strain.

Next, an antifungal activity spectrum of the present strain against 10 strains of the mold was measured. This measurement was conducted after incubated the milk agar plate at 30° C. (centigrade) for 5 days. Consequently, it was confirmed that the present strain had the antifungal activity against three bacteria strains of genus *Penicillium* that had a bad influence on a feed, that is, *Penicillium chrysogenum* (JCM2056), *Penicillium olsonii* (wild type) and *Penicillium roqueforti* (PR-1). Among them, it was confirmed that the *Penicillium chrysogenum* (JCM2056) was perfectly controlled and restrained from growth.

[Examination Case No. 4 of Antifungal Activity]

Temporal changes of antifungal activity (Examination Case No. 4) and pH in a 10% skim milk of the present strain were examined by a colony plate count method. A line graph (three lines) in FIG. 4 shows pH of the skim milk. A first line having triangular points shows the temporal change of the pH of the skim milk that inoculated only the present strain. A second line (uppermost line) having rhomboid points shows the temporal change of the pH of the skim milk that inoculated only the *Penicillium roqueforti* PR-1 strain. A third line (line generally overlapped with the first line) having circular points shows the temporal change of the pH of the skim milk that inoculated both the *Penicillium roqueforti* PR-1 strain and the present strain. As shown in the line graph in FIG. 4, the pH goes down in the skim milk that inoculated only the present strain and in the skim milk that inoculated both the *Penicillium roqueforti* PR-1 strain and the present strain. However, there was not found any decrease in the pH of the skim milk that inoculated only the *Penicillium roqueforti* PR-1 strain.

A bar graph (three bars) in FIG. 4 shows a number of the bacteria in the present strain and the PR-1 strain. The bar graph at a left side shows the number of the bacteria of the present strain that was incubated solo. The graph at a center shows the number of the bacteria in the PR-1 strain that was incubated solo. The bar graph at a right side shows the number of the PR-1 strain when added with the present strain. As shown by the bar graph in FIG. 4, the PR-1 strain when added with the present strain was controlled and strained from propagation, and no residual bacterial count of the PR-1 strain was detected after 36 hours. Hence, it is obvious that the present strain is preferably applicable even to a dairy product (fermented food) such as yoghurt or the like, for example.

[Examination Case No. 5 of Antifungal Activity]

A feed for egg-laying hens added with the present strain and a feed for egg-laying hens added with no present strain were left out for one year, respectively. Then, generation states of mold were checked. In FIG. 5, a picture image at a left side shows the generation state of the mold in case of adding no present strain in the feed for egg-laying hens. A picture image of a right side in FIG. 5 shows the generation state of the mold in case of adding the present strain to the feed for egg-laying hens. As shown in FIG. 5, the feed for egg-laying hens added with no present strain gets moldy and totally decomposed. However, no mold generation is confirmed on the feed added with the present strain, and the same feed is not decomposed. Moreover, as shown in FIG. 6, when the contamination mold is separated for observation from the feed for egg-laying hens that had no present strain added and got rotted, a conidiophore or conidiospores lined up behind each other like four sterigmas. Hence, this mold was identified as the *Penicillium olsonii* from the results of its configuration, grown in a selection medium and taxonomic characteristics. By such results, it was confirmed that the present strain had a strong control effect on the growth of the *Penicillium olsonii*.

[Examination Case No. 6 of Antifungal Activity]

Antifungal activity of the present strain against the *Penicillium roqueforti* PR-1 was examined in the same manner as the examination case No. 3. Growth states of the PR-1 strain were observed in the test plate (culture medium incubating the PR-1 strain added with the present strain) and in the control plate (culture medium incubating the PR-1 strain solo). The incubation was carried out at 30° C. (centigrade) for 5 days. Consequently, as shown in an upper side picture image (A) in FIG. 7, many growths of the PR-1 strain were observed in the culture medium containing no present strain. On the one hand, as shown a lower side picture image (B) in FIG. 7, only the present strain could be observed and no growth of the PR-1 strain could not be observed in the culture medium containing the present strain.

[Examination of Deodorizing Function of Excretory Substance of Domestic Fowl and Domestic Animal]

Ammonia concentrations were measured in a pig house, a chicken coop and a cow barn, odor eliminating, respectively, so as to examine a deodorizing function of the present bacteria as follows.

[Example for Pig Feed (Second Practical Example)]

As a second comparative example, there was prepared a pig feed (60 wt % of cereal (corn, rye), 26 wt % of oil-seed cake and meal, 2 wt % of chaff and bran and 12 wt % of other substances (sweet stuff waste, molasses, calcium phosphate or the like) added with 0.2 wt % of *bacillus natto*. Then, the pig feed of the second comparative example was served for a fixed time period for ingestion to 2000 pigs in total that were bred in a breeding house for postweaning little pigs, a rearing house and a mother pig house, respectively. Thereafter, the ammonia concentrations were measured in the pig houses after the same period had passed. The ammonia concentrations were measured by installing an ammonia gas detector tube (manufactured by GASTEC CORPORATION, 3DL) at a height of 1.5 m in the pig houses.

On the other hand, there was prepared a feed by adding the living lactic acid bacterial agent obtained by the aforementioned manufacturing method to the aforesaid pig feed so that each pig could ingest 4 g (2.12*1010) per day as a second practical example. Then, the pig feed of the second practical example was served for ingestion to each of the aforementioned 2000 pigs after the breeding period by the pig feed of the second comparative example had passed. Thereafter, the ammonia concentrations were measured after 20 days and 40 days from after the breeding period by the pig feed of the second comparative example had passed, respectively, in the same manner as the second comparative example. In other words, the test of the second practical example was conducted after the test of the second comparative example was finished. As a result, as shown in Table 2, the second practical example shows a significant deodorizing function in comparison with the second comparative example. In particular, ammonia odor was scarcely generated after 40 days.

TABLE 2

|  | Ammonia concentration (ppm) | | |
| --- | --- | --- | --- |
|  | 2nd comparative example | 2nd practical example | |
|  |  | 20 days after | 40 days after |
| Postweaning little pig breeding house | 32.6 | 8.67 | ND (not more than detection limit) |
| Rearing house | 27 | 8.11 | 2.5 |
| Mother pig house | 16.1 | 0.7 | ND (not more than detection limit) |

[Practical Example for Feed for Egg-Laying Hens (Third Practical Example)

As a third comparative example, there was prepared a feed for egg-laying hens (59 wt % of corn, 23 wt % of oil-seed cake and meal, 3 wt % of chaff and bran, 1 wt % of animal-based feed (fish meal) and 14 wt % of other substances (calcium carbonate, animal oil and fat, corn steep liquor or the like) added with 2.0 wt % of a commercially available lactic acid bacteria material (composed of lactic acid bacteria, yeast, filamentous bacteria or fungi or the like, made by A Corporation). Then, the feed for egg-laying hens of the third comparative example was served for a fixed time period for ingestion to 12000 egg-laying hens (ISA Brown). Thereafter, the ammonia concentration was measured in the hen house.

On the other hand, there was prepared a feed by adding 1.0 wt % of the living lactic acid bacterial agent obtained by the aforementioned manufacturing method to the feed for egg-laying hens similar to the aforementioned as a third practical example. Then, the feed for egg-laying hens of the third practical example was served for ingestion to each of the aforementioned 12000 hens (ISA Brown) after the breeding period by the feed for egg-laying hens of the third comparative example had passed. Thereafter, the ammonia concentration in the hen house was measured. Results were shown in Table 3.

Moreover, the same feed for egg-laying hens as the third embodiment was served for a fixed time period for ingestion to the aforementioned 12000 egg-laying hens (ISA Brown) after the breeding period by the feed for egg-laying hens of the third comparative example had passed. The ammonia concentrations in the hen house were measured after the test started, that is, after 5 day, 18 days, 25 days and 37 days after the living lactic acid bacterial agent was added. Results were shown in Table 4. Here, in the third comparative example and the third practical example, the measurement of the ammonia concentrations were carried out by the same measuring method and the measuring device as the aforementioned second practical example. Moreover, the test of the third practical example was conducted over 15 months after the test of the third comparative example was conducted over 15 months and an additive-free feed for egg-laying hens was then served for three months for ingestion of the egg-laying hens. Furthermore, in each of the tests of the third comparative example and the third practical example, the breeding conditions were made the same in order to adjust comparison conditions. For example, a wing number per chicken coop (area per one chicken) and a chicken coop environment (equipment or the like) were made the same. On the other hand, a time lag was set for the breeding period in the form of a prior period and a latter period as mentioned above. Table 3 shows an average value of results that were periodically measured between the examination periods of each 15 months of the third comparative example and the third practical example. As a result, as shown in Table 3, the deodorizing or odor eliminating function of the present bacteria was superior even in case of the domestic fowls. Moreover, as shown in Table 4, the odor eliminating effect increased with time. Furthermore, better values were acquired in case of breeding by the feed for egg-laying hens of the third practical embodiment in comparison with the third comparative example, in any of a survival rate (87.39% to 52.07%, improvement of 35.32%) and an egg production (3,698,683 to 3,389,253, increase of 309,430).

TABLE 3

|  | Ammonia concentration (ppm) | |
| --- | --- | --- |
|  | 3rd comparison example | 3rd practical example |
| In chicken house | 19.8 | 3.0 |

TABLE 4

| Before adding present strain | Ammonia concentration (ppm) 3rd practical example | | | |
| --- | --- | --- | --- | --- |
|  | 5 days after | 18 days after | 25 days after | 37 days after |
| 23.00 | 10.8 | 3.00 | 4.36 | 1.79 |

[Practical Example for Milk Cow Feed (Fourth Practical Example)]

As a fourth comparative example, there was prepared a milk cow feed (5 kg of corn, 3 kg of barley, 1.5 to 2.0 kg of beet, 2 kg of cotton seeds, 1.2 to 1.3 kg of defatted soybeans, 0.8 kg to 1 kg of soybeans, 8 to 10 kg of hay and 150 to 200l of water) added with a commercially available lactic acid bacterial material (composed of lactic acid bacteria, yeast, koji mold or the like, made by B Corporation) so that each of the milk cows could ingest 200 g per day. Then, the milk cow feed of the fourth comparative example was served for a fixed time period for ingestion to 130 milk cows (Holstein). Thereafter, the ammonia concentration was measured in a cow barn.

On the other hand, there was prepared a feed by adding the living lactic acid bacterial agent obtained by the aforementioned manufacturing method to the milk cow feed similar to the aforesaid feed so that each milk cow could ingest 40 g per day as a fourth practical example. Then, the milk cow feed of the fourth practical example was served for a fixed time period for ingestion to each of the aforementioned 130 milk cows. Thereafter, the ammonia concentration was measured in the cow barn. The test of the fourth practical example was conducted after having each of the aforementioned 130 milk cows ingest an additive-free milk cow feed for a fixed time period after finishing the test of the fourth comparative example. The measurement of the ammonia concentrations were carried out by the same measuring method and the measuring device as the aforementioned second practical example. As a result, as shown in Table 5, the deodorizing effect was superior even in case of the milk cow.

TABLE 5

| | Ammonia concentration (ppm) | |
| --- | --- | --- |
| | 4th comparison example | 4th practical example |
| In cow barn | 5.52 | ND (not more than detection limit) |

[Examination of Egg-Laying Hen's Survival Rate and Egg-Laying Rate]

In the test over each 15 months carried out in the examination of the deodorizing effect of the above-mentioned third practical example, a survival rate and an egg-laying rate were also examined together with the test of the deodorizing function. As described above, the third comparative example 3 had the domestic fowls ingest the domestic fowl feed added with the commercially available lactic acid bacterial material. On the other hand, as described above, the third practical example had the domestic fowls ingest the domestic fowl feed added with the living lactic acid bacterial agent. As a result, as shown in Table 6, the survival rate of the egg-laying hens that ingested the present bacteria was very high. Moreover, as shown in Table 7, the egg-laying hens that ingested the present bacteria were also excellent in the egg-laying rate.

TABLE 6

| | Survival rate (%) |
| --- | --- |
| 3rd practical example | 87.39 |
| 3rd comparative example | 52.07 |

TABLE 7

| | Total egg production (number) | Egg-laying rate (%) |
| --- | --- | --- |
| 3rd practical example | 3,698,683 | 100 |
| 3rd comparative example | 3,389,253 | 91.6 |

[Examination of Improving Function of Milk Quality (Fifth Practical Example)]

Milk cows were bred by using a milk cow feed (Fifth Comparison Example) similar to the feed (Fourth Comparison Example) that added the commercially available lactic acid bacterial material to the milk cow feed in the examination of the deodorizing function of the aforementioned fourth practical example and a milk cow feed (Fifth Practical Example) similar to the feed (Fourth Practical Example) that added the living lactic acid bacterial agent obtained by the manufacturing method to the milk cow feed, respectively. Then, the milk cows were milked 17 times at intervals of ten days. Thereby, examination was performed on a milk fat percentage, a milk protein percentage and a non-fat milk solid content percentage of the milk. In the fifth comparative example, 130 milk cows (Holstein) were served for ingestion with the milk cow feed added with the commercially available lactic acid bacterial material. Moreover, the test of the fifth practical example was conducted by having the milk cows ingest an additive-free milk cow feed for a fixed time period after finishing the test of the fifth comparative example and thereafter by having the same 130 milk cows (Holstein) ingest the milk cow feed (feed of the fifth practical example) added with the living lactic acid bacterial agent obtained by the manufacturing method. The milk fat percentage, the dairy protein percentage and the non-fat milk solid of each milk milked from the milk cows were measured by use of a milk constituent analyzing device (Milko Scan FT120 manufactured by FUJIHIRA INDUSTRY CO., LTD.). Table 8 shows an average of 17 time measurement values which went through the test. As a result, as shown in Table 8, the milk fat percentage, the milk protein percentage and the non-fat milk solid content percentage of the milk produced from the milk cows that ingested the present bacteria were all high compared with the case of the fifth comparative example and its milk quality was improved.

TABLE 8

| | Milk fat percentage (%) | Milk protein percentage (%) | Non-fat Milk solid content percentage (%) |
| --- | --- | --- | --- |
| 5th practical example | 4.01 | 3.41 | 9.00 |
| 5th comparative example | 3.91 | 3.29 | 8.82 |

From the above results, it is thought that the present bacteria is highly fixable in intestines of domestic fowls or livestock so as to improve digestion and absorption thereby to have the probiotic activity even when the present bacteria is used solo. Therefore, the present invention can be concretized as the probiotics (living microorganism agent) and exhibits the above-mentioned effects. Moreover, as described above, the present invention can be embodied not only into the animal feed additive but also into the animal feed added with the present strain or the animal drink added with the present strain. In this case, the present invention performs the same effects as the above. Furthermore, as described above, the present strain has the effects on improvement of the animal breeding such as the livestock or the domestic fowls. In addition, if the present strain is added to foods, it is also applicable to a use for the preservation of foods or food microorganism control (biopreservation). In this case, the present strain performs such a proper effect as not seen conventionally by the property or the characteristic as mentioned above. Moreover, as described in the examination case No. 4 of the aforementioned antifungal activity, the present strain can be added to fermented foods so as to be used for manufacturing of the fermented foods. Thus, the present strain performs such a proper effect as not seen conventionally by the property or the characteristic as mentioned above. In addition, the animal feed or the like added with the present strain may be dispersed intentionally or spread unintentionally on a ground, a floor, a drain ditch or the like of a stable or the like at the time of feeding to the animals or the like. Then, the present strain controls the microorganisms at such dispersed places. Thereby, the present strain cleans up or deodorizes the dispersed places by the above-mentioned property or characteristic so as to perform the proper effects that has not been seen conventionally. Alternatively, the animal feed or the like added with the present strain may be dispersed directly in the water or be sunk and deposited in the water while being housed in a permeable case such as a net-shaped object. Then, the present strain controls the microorganisms in the water. Thereby, the present strain purifies or disinfects the water by the above-mentioned property or characteristic so as to perform the proper effects that has not been seen conventionally.

The invention claimed is:
1. A biologically pure culture of *Lactobacillus delbrueckii* ANTI MUFFA deposited under FERM BP-10663.

2. A feed for animals, comprising *Lactobacillus delbrueckii* ANTI MUFFA deposited under FERM BP-10663.

3. A drink for animals, comprising *Lactobacillus delbrueckii* ANTI MUFFA deposited under FERM BP-10663.

4. An agent having an antifungal activity comprising *Lactobacillus delbrueckii* ANTI MUFFA deposited under FERM BP-10663 as a living lactic acid bacteria.

5. An additive for an animal feed, comprising *Lactobacillus delbrueckii* ANTI MUFFA deposited under FERM BP-10663 as an active ingredient.

6. A method of feeding animals, comprising:
orally administering to animals *Lactobacillus delbrueckii* ANTI MUFFA deposited under FERM BP-10663.

7. A method of feeding animals as recited in claim 6, in which said administering improves deodorization of an excretory substance of animals.

8. A method of feeding animals as recited in claim 6, in which said administering improves a survival rate of animals.

9. A method of feeding animals as recited in claim 6, in which said administering improves an egg-laying rate of hens for egg collection.

10. A method of feeding animals as recited in claim 6, in which said administering improves milk quality of milk cows to which *Lactobacillus delbrueckii* ANTI MUFFA has been administered.

11. A method of preserving a fermented food, comprising:
adding to a fermented food *Lactobacillus delbrueckii* ANTI MUFFA deposited under FERM BP-10663.

12. A method of cleaning the floor or ground of a stable for animals, comprising:
dispersing *Lactobacillus delbrueckii* ANTI MUFFA deposited under FERM BP-10663 on a floor or a ground of the stable.

13. A method of cleaning water, comprising:
dispersing *Lactobacillus delbrueckii* ANTI MUFFA deposited under FERM BP-10663 directly into the water to be cleaned.

14. A method of cleaning water, comprising:
adding *Lactobacillus delbrueckii* ANTI MUFFA deposited under FERM BP-10663 in a water permeable case; and
immersing the water permeable case into the water to be cleaned.

* * * * *